United States Patent [19]
Chen

[11] Patent Number: 5,776,076
[45] Date of Patent: Jul. 7, 1998

[54] SAFETY VACUUM SYRINGE FOR BLOOD SAMPLING

[76] Inventor: Long-Hsiung Chen, 5F, No. 91-3, Chung Cheng Rd., Sec. 4, Taipei, Taiwan

[21] Appl. No.: 614,003

[22] Filed: Mar. 11, 1996

[51] Int. Cl.[6] .................................................. A61M 5/00
[52] U.S. Cl. ......................... 600/573; 604/110; 604/164
[58] Field of Search ............................. 604/110, 164; 600/573, 576, 577, 578, 583

[56] References Cited

U.S. PATENT DOCUMENTS

| | | | |
|---|---|---|---|
| 3,886,930 | 6/1975 | Ryan | 128/766 |
| 4,758,231 | 7/1988 | Haber et al. | 128/763 |
| 4,838,863 | 6/1989 | Allard et al. | 604/110 |
| 4,950,241 | 8/1990 | Ranford | 604/110 |
| 4,976,925 | 12/1990 | Porcher et al. | 604/110 |
| 5,069,225 | 12/1991 | Okamura | 128/765 |
| 5,423,758 | 6/1995 | Shaw | 604/110 |

*Primary Examiner*—Aaron J. Lewis
*Assistant Examiner*—V. Srivastava
*Attorney, Agent, or Firm*—Rosenberg, Klein & Bilker

[57] ABSTRACT

A safety vacuum syringe for blood sampling, which includes a barrel, a cylindrical vacuum container mounted inside the barrel, a reduced tubular lining cap mounted in the barrel at the front end, a hollow cylindrical connecting member fixedly secured to the front end of the cylindrical vacuum container, a needle holder having an outer needle cannula and an inner needle cannula at two opposite ends, an outer needle cap covered on the outer needle cannula, and an outer bottom cap fastened to the barrel to hold the vacuum container on the inside, wherein when the vacuum container is pulled out and detached from the barrel, the connecting member and the needle holder are pulled to the inside of the barrel, the outer needle cap and the outer bottom cap are respectively and invertedly inserted into the two opposite ends of the barrel to deform the needle cannulas in the barrel.

6 Claims, 6 Drawing Sheets

SAFETY VACUUM SYRINGE FOR BLOOD SAMPLING

BACKGROUND OF THE INVENTION

The present invention relates to vacuum syringes for blood sampling, and relates more particularly to such a safety vacuum syringe in which the needle holder with the two opposite needle cannulas are pulled to the inside of the barrel after the sampling of blood so that the needle cannulas are deformed when the outer needle cap and the outer bottom cap are respectively and invertedly inserted into the two opposite ends of the barrel.

In order to prevent contamination after the use of disposable hypodermic syringes, used disposable hypodermic syringes must be properly disposed of. Various safety hypodermic syringes have been disclosed, and have appeared on the market. Exemplars of these safety hypodermic syringes are seen in Taiwan patent utility model No. 84873; U.S. Pat. No. 5,328,475. These safety hypodermic syringes permit the needle holder with the needle cannula to be pulled to the inside of the barrel and then deformed. However, even the needle cannula is deformed, it still will slip to the outside of the barrel when the barrel is oscillated or broken. Further, the safety designs of conventional safety hypodermic syringes are not applicable for the production of vacuum syringes for blood sampling because regular vacuum syringes commonly have a double-needle structure, i.e., the needle holder holds an outer needle cannula on the outside for insertion into the blood vessel, and an inner needle cannula on the inside for insertion into the vacuum chamber of the vacuum container.

SUMMARY OF THE INVENTION

The present invention has been accomplished under the circumstances in view. It is one object of the present invention to provide a safety vacuum syringe for blood sampling which permits the needle holder with the outer needle cannula and the inner needle cannula to be pulled to the inside of the barrel after the use of the vacuum syringe. It is another object of the present invention to provide a safety vacuum syringe for blood sampling which permits the outer needle cap and the outer bottom cap to be respectively detached from the barrel and then invertedly inserted into the two opposite ends of the barrel to collapse the outer needle cannula and the inner needle cannulla. It is still another object of the present invention to provide a safety vacuum syringe for blood sampling which permits the outer needle cap and the outer bottom cap to be respectively and invertedly inserted into the two opposite ends of the barrel to reinforce the strength of the barrel and to protect it against outside pressure after the use of the safety vacuum syringe. It is still another object of the present invention to provide a safety vacuum syringe for blood sampling which permits the outer needle cap and the outer bottom cap to be respectively fastened to the two opposite ends of the barrel so that the safety vacuum syringe can be conveniently disposed of after its use.

DETAILED DESCRIPTION OF THE PREFERRED EMBODIMENT

Figure 1:
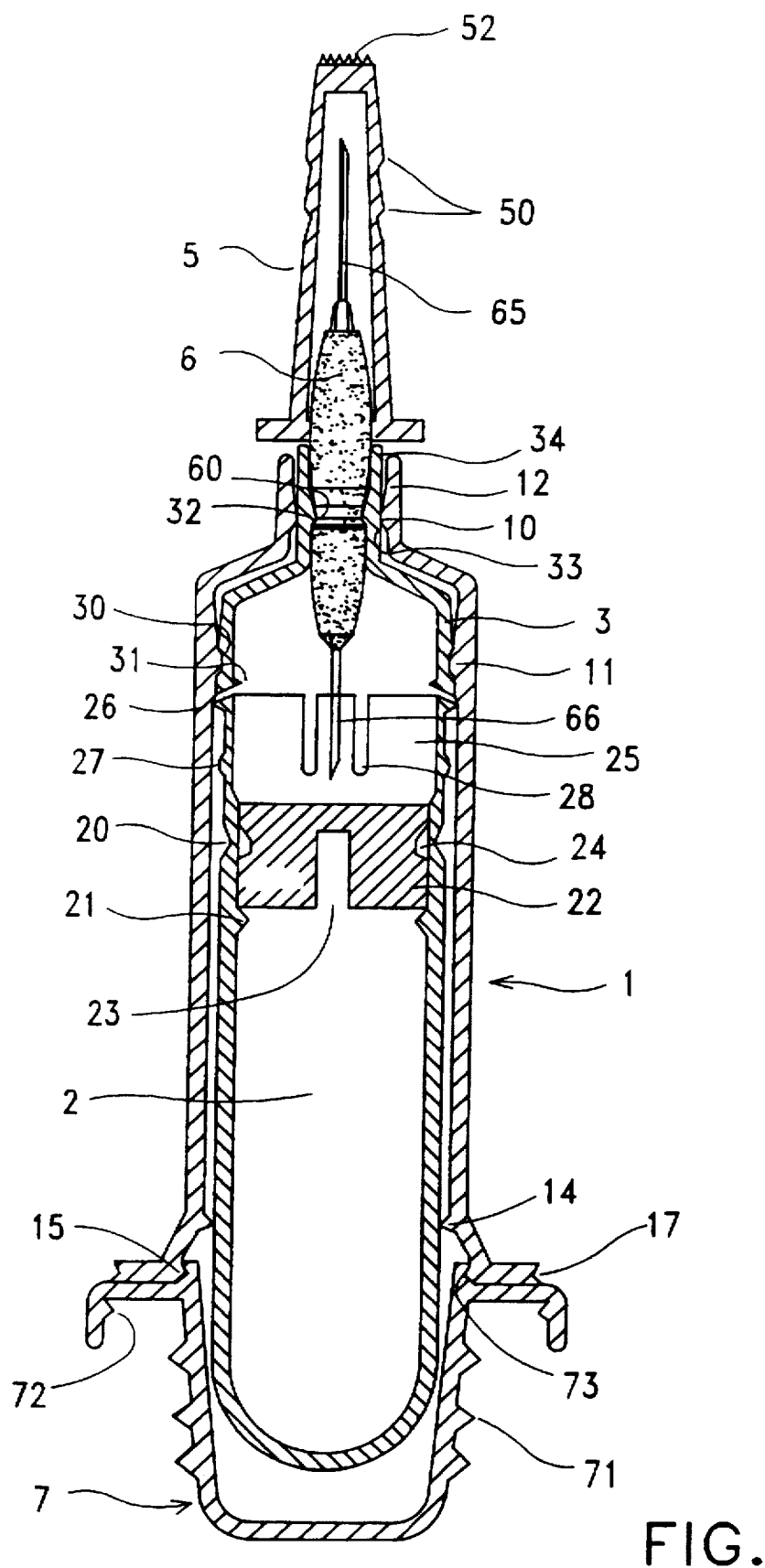
FIG. 1 is a sectional view of a safety vacuum syringe for blood sampling according to the present invention.

Referring to FIG. 1, a barrel 1 has a reduced tubular front end 12 and a flared opening bottom end with an outward flange 17 and an inwardly projected fastening ring 15 thereat, and an inward annula flange 14 disposed over the flared opening near the bottom. A cylindrical vacuum container, referenced by 2, has an inside annular groove 21 raised around the inside wall at a suitable location. A rubber stopper 22 is mounted inside the cylindrical vacuum container 2 and stopped at the inside annular groove 21 to keep the inside of the cylindrical vacuum container 2 in a vacuum condition. The rubber stopper 22 is made of cylindrical shape having a rounded blind hole 23 at the center of the bottom side, which diminishes the thickness of the center area of the rubber stopper 22 so that the inner needle cannula 66 of hollow needle holder, referenced by 6, can be easily inserted through the rubber stopper 22 into the inside vacuum space of the cylindrical vacuum container 2. The cylindrical vacuum container 2 has a neck 20 in front of the inside annular flange 21. When blood sample is collected, the cylindrical vacuum container 2 can be broken easily at the neck 20 and then removed from the barrel 1. The rubber stopper 22 has an outside annular groove 24 around the periphery corresponding to the neck 20 of the cylindrical vacuum container 2. When the cylindrical vacuum container 2 is broken at the neck and removed from the barrel 1, the rubber stopper 22 is still retained to the detached cylindrical vacuum container 2 to seal sampled blood on the inside. However, the rubber stopper 22 can be easily removed from the detached cylindrical vacuum container 2 through the outside annular groove 24, permitting sampled blood to be poured into a test tube for examination.

Figure 2:
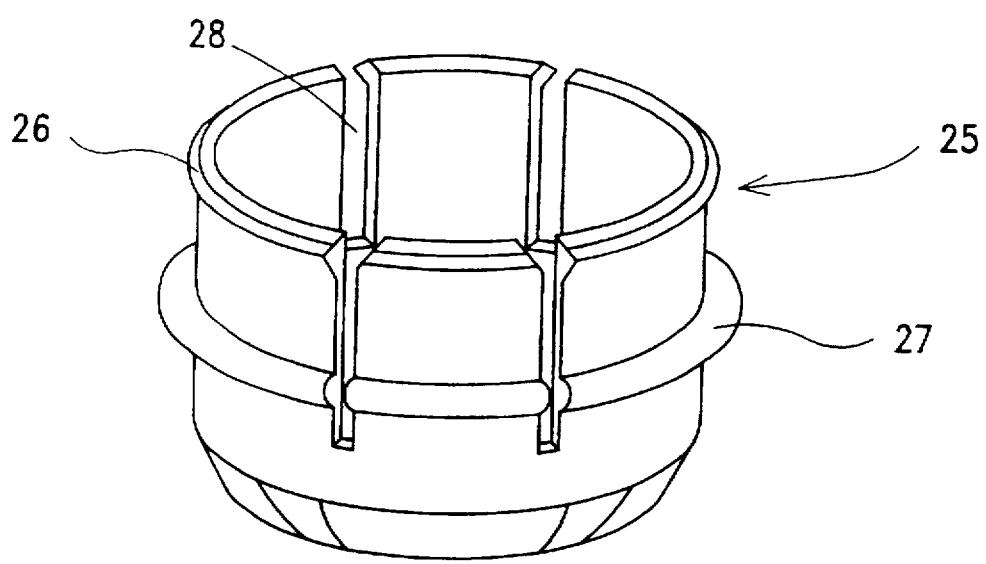
FIG. 2 is a perspective view of a hollow cylindrical connecting member according to the present invention.

Referring to FIG. 2 and FIG. 1 again, a hollow cylindrical connecting member 25 is connected to the cylindrical vacuum container 2 and the rubber stopper 22 at the front side, having a plurality of longitudinal splits 28 extending to the front side, a downwardly sloping outside top flange 26 raised around the periphery of the top end, and an outside annular flange 27 raised around the periphery in the middle. The longitudinal splits 28 enable the connecting member 25 to be compressed inwards and forced into the inside of a reduced tubular lining cap 3 when the cylindrical vacuum container 2 is pushed forwards in the barrel 1. The reduced tubular lining cap 3 has an outside annular groove 30, an inward bottom flange 31 raised around the periphery of the bottom end and sloping upwardly inwards, a first inside annular flange 32, an outside annular flange 33, and a second inside annular flange 34. By engaging the outside annular groove 30 and the outside annular flange 33 with respective smoothly curved inside annular flanges 11, of the barrel 1, the lining cap 3 is firmly retained to the reduced tubular front end 12 of the barrell 1 on the inside. The needle holder 6 is mounted in the reduced portion of the lining cap 3, having an outside annular groove 60 around the periphery, which works with the first inside annular flange 32 and second inside annular flange 34 of the lining cap 3 for positioning. The aforesaid inner needle cannula 66 is connected to the needle holder 6 at one end and suspending in the hollow cylindrical connecting member 25. An outer needle cannulla 65 is connected to the needle holder 6 at an opposite end and projecting out of the lining cap 3. An outer needle cap 5 is detachably fastened to the needle holder 6 outside the barrel 1 and the reduced tubular lining cap and covered over the outer needle cannula 65, formed of a tapered pipe having a plurality of outside annular grooves 50 around the periphery at different elevations, and a top head 52 disposed to a small closed end thereof. The top head 52 can be serrated, or made of flat shape of certain thickness. An outer bottom cap 7 is also formed of a tapered pipe gradually smaller toward a closed end having a plurality of outside annular grooves 71 at different elevation fastened to the bottom end of the barrel 1 to hold the cylindrical vacuum container 2 on the inside, having an outside annular groove 73 at an opening end engaged with the inwardly projected fastening ring 15 of the outward bottom flange 17 of the barrel 1 and a reversely folded flange 72 on a bottom end thereof.

Figure 3:
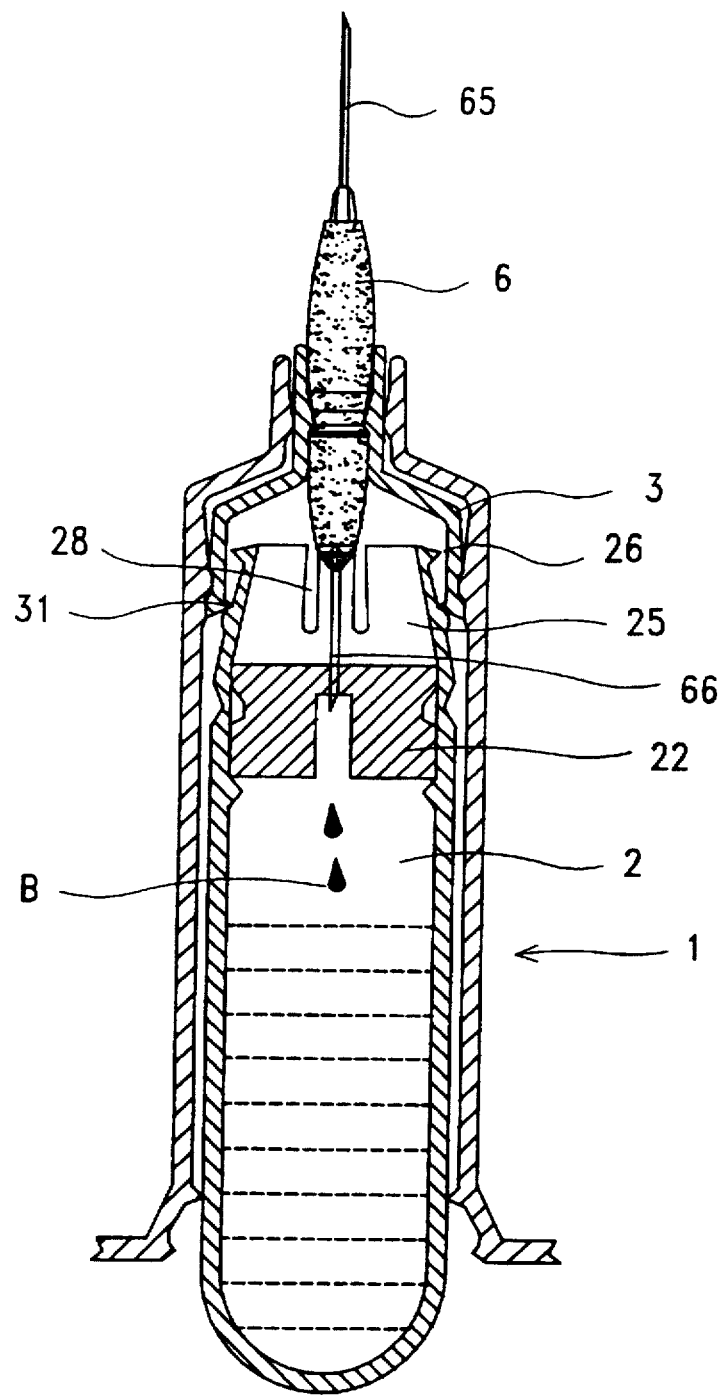
FIG. 3 shows the outer needle cap and the outer bottom cap respectively removed from the needle holder and the barrel, and blood drawn into the cylindrical vacuum container according to the present invention.

Referring to FIG. 3, when to collect blood sample, the needle cap 50 and the outer bottom cap 7 are respectively removed from the needle holder 6 and the barrel 1, then the outer needle cannula 65 is inserted into the patient's blood vessel, and then the cylindrical vacuum container 2 is pushed forwards in the barrell 1. When the cylindrical vacuum container 2 is pushed forwards in the barrel 1, the outside top flange 26 is compressed inwards by the inwardly bottom flange 31 and forced into the inside of the lining cap 3, causing the inner needle cannula 66 to pierce the rubber stopper 22 and to enter the inside of the cylindrical vacuum container 2. When the inner needle cannula 66 passes to the inside of the cylindrical vacuum container 2, blood B is sucked from the blood vessel into the cylindrical vacuum container 2 through the outer needle cannula 65 and the inner needle cannula 66.

Figure 4:
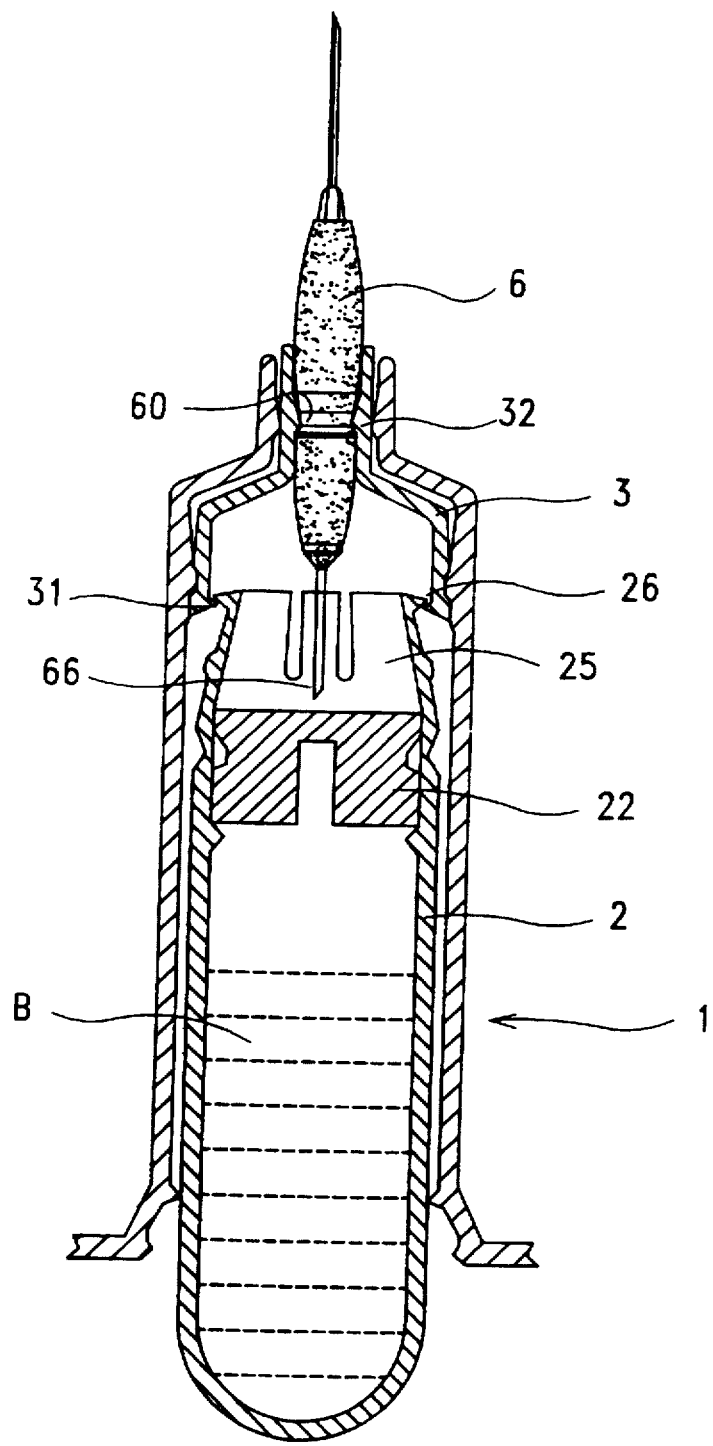
FIG. 4 shows the connecting member with the cylindrical vacuum container pulled backwards, and the outside top flange of the connecting member engaged with the inward bottom flange of the inner cap according to the present invention.

Referring to FIG. 4, when blood B is collected in the cylindrical vacuum container 2, the outer needle cannula 65 is removed from the blood vessel, then the cylindrical vacuum container 2 is pulled backwards. When the cylindrical vacuum container 2 is pulled backwards, the outside top flange 26 of the cylindrical vacuum container 2 will be stopped at the inward bottom flange 31 of the lining cap 3. When the outside top flange 26 of the cylindrical vacuum container 2 is stopped at the inward bottom flange 31 of the lining cap 3, the inner needle cannula 66 is disconnected from the rubber stopper 22. When keep pulling the cylindrical vacuum container 2 backwards, the outside annular groove 30 and outside annular flange 33 of the lining cap 3 will be disengaged from the smoothly curved inside annular flanges 10, 11 of the barrel 1, permitting the lining cap 3 with the needle holder 6 to be carried backwards by the cylindrical vacuum container 2. When the cylindrical vacuum container 2 is continuously pulled backwards, the outside annular flange 27 of the connecting member 25 will be stopped at the inside bottom flange 14 of the barrel 1.

Figure 5:
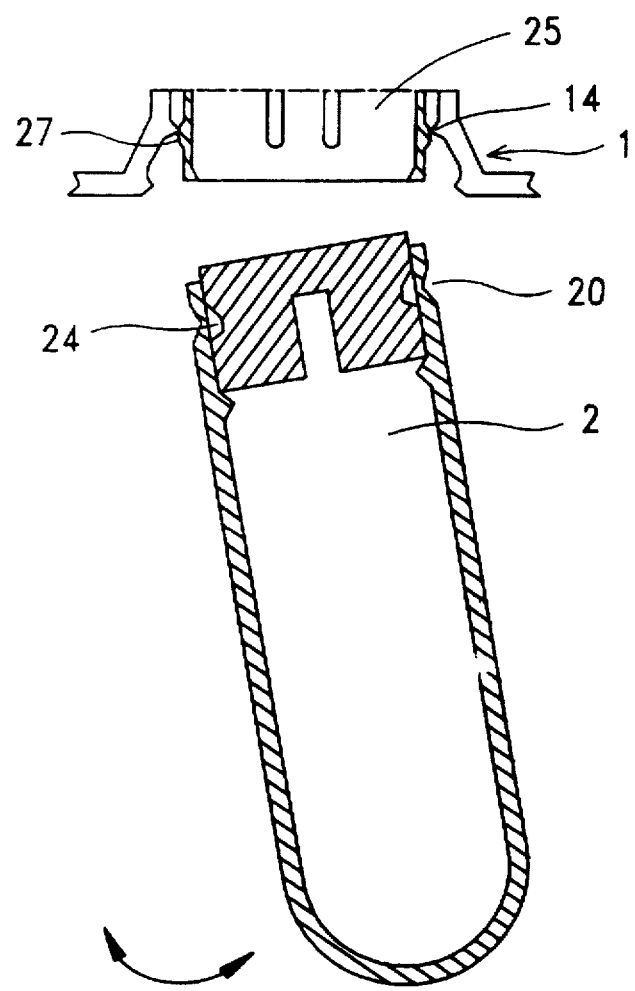
FIG. 5 shows the cylindrical vacuum container disconnected from the connecting member according to the present invention.

Referring to FIG. 5, when the cylindrical vacuum container 2 is pulled out of the barrel 1 and the outside annular flange 27 of the connecting member 25 is stopped at the inside bottom flange 14 of the barrel 1, the cylindrical vacuum container 2 is broken at the neck 20 by force. When the cylindrical vacuum container 2 is disconnected from the connecting member 25, the connecting member 25 with the lining cap 3 and the needle holder 6 are retained inside the barrel 1 (see also FIG. 6).

Figure 6:
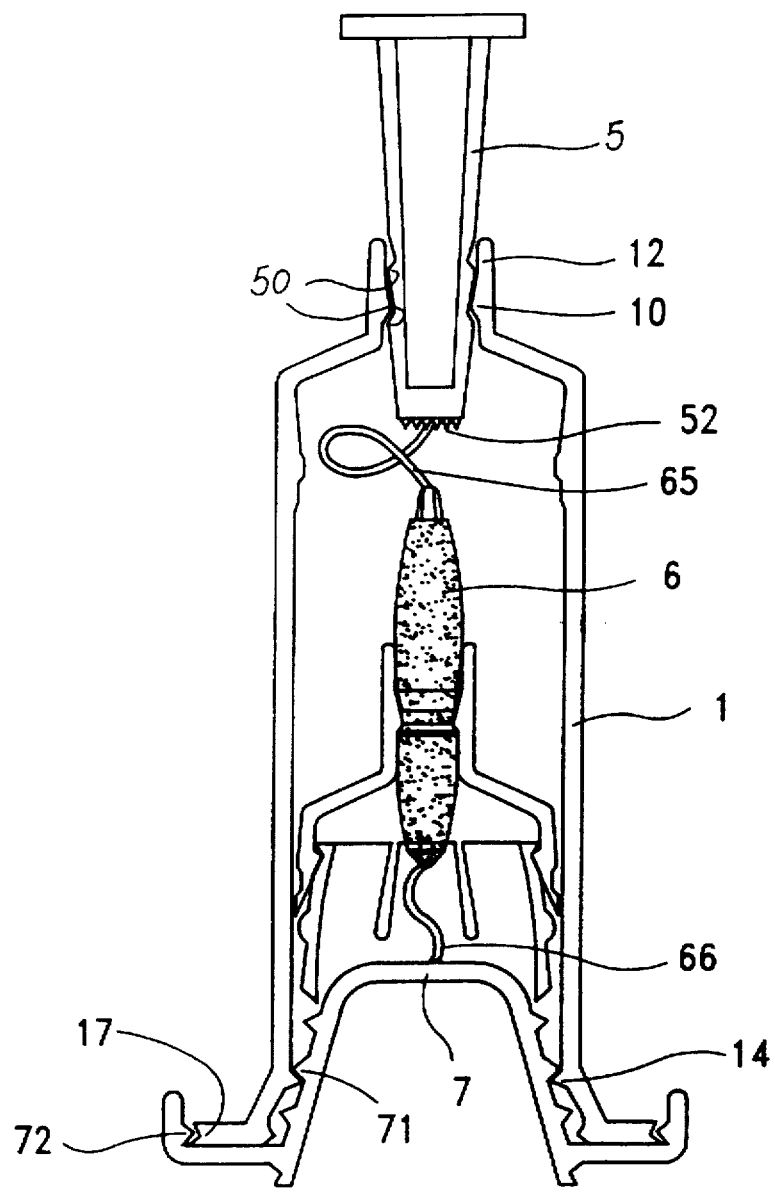
FIG. 6 shows the outer needle cap and the outer bottom cap respectively fastened to the two opposite ends of the barrel, and the needle cannulas deformed.

Referring to FIG. 6, after the removal of the cylindrical vacuum container 2, the outer needle cap 5 is turned upside down, and inserted into reduced tubular front end 12 of the barrel 1 and the top head 52 is stopped against the outer needle cannula 65 by a certain thickness or serrated surface thereof and then forced into the front end of the barrel 1. When the top head 52 of the outer needle cap 5 is inserted into the front end of at least one of the plurality of barrel 1, the outside annular grooves 50 of the outer needle cap 5 will be engaged with the inside annular flange 10 in the reduced tubular front end of the barrel 1, and therefore the outer needle cap is stopped by the front end of the barrel 1. Then the outer bottom cap 7 is invertedly inserted into the bottom end of the barrel 1. When the outer bottom cap 7 is invertedly inserted into the bottom end of the barrel 1, a plurality of outside projecting portions 71, and a reversely folded flange of the outer bottom cap 7 are respectively forced into engagement with the inward annual flange 14 and the outward bottom flange 17 of the barrel 1, and at the same time, the outer needle cannula 65 and inner needle cannula 66 are forced to deform between the outer needle cap 5 and the outer bottom cap 7. When the outer needle cap 5 and the outer bottom cap 7 are respectively inserted into two opposite ends of the barrel 1, invertedly they support the barrel 1 against outside pressure. Therefore, the barrel 1 will not be broken easily. Because the outer needle cap 5 and the outer bottom cap 7 are respectively fastened to the barrel 1 after the use of the vacuum syringe, the used vacuum syringe can be conveniently and safely disposed of.

It is to be understood that the drawings are designed for purposes of illustration only, and are not intended as a definition of the limits and scope of the invention disclosed.

What the invention claimed is:

1. A safety vacuum syringe for blood sampling, comprising:

a barrel having a reduced tubular front end, a flared opening bottom end, an outward flange and an inward projected fastening ring disposed to said bottom end, and an inward annular flange disposed inside the flared opening near said inward projected fastening ring;

a cylindrical vacuum container mounted inside said barrel, said cylindrical vacuum container having a neck and a rubber stopper sealed at said neck;

a reduced tubular lining cap mounted in said reduced tubular front end of said barrel, said reduced tubular lining cap having an inward bottom flange around a bottom end thereof;

a hollow cylindrical connecting member fixedly connected to a front end of said cylindrical vacuum container outside said rubber stopper and disposed adjacent to said reduced tubular lining cap, said connecting member having a plurality of longitudinal splits, an annular flange raised outwardly around a periphery at a middle thereof, and an outside top flange disposed on a top end thereof, a needle holder fastened in said reduced tubular lining cap, having an outer needle cannula at a front end outside said barrel, and an inner needle cannula at the opposite end suspending in said hollow cylindrical connecting member;

an outer needle cap covered on said needle holder over said outer needle cannula; and an outer bottom cap fastened to the bottom end of said barrel to hold said cylindrical vacuum container inside said barrel, said outer bottom cap having an outside annular groove detachably engaged with said inward projected fastening ring of said barrel;

characterized that said outer needle cap and said bottom cap are formed of a tapered pipe gradually small toward a closed end thereof so as to be able to invertedly be inserted into said reduced tubular front end and said flared opening bottom end of said barrel respectively for deforming said outer needle cannula and said inner needle cannula in said barrel.

2. The safety vacuum syringe for blood sampling of claim 1 wherein said outer needle cap has a flat top head of certain thickness.

3. The safety vacuum syringe for blood sampling of claim 1 wherein said outer needle cap has a serrated top head.

4. The safety vacuum syringe for blood sampling of claim 1 wherein said outer needle cap has a plurality of outside annular grooves, which are forced into engagement with said inside annular flange inside reduced tubular front end of said barrel to prevent disconnection of said outer needle cap from said reduced tubular front end of said barrel after the insertion of said outer needle cap into said reduced tubular front end of said barrel invertedly.

5. The safety vacuum syringe for blood sampling of claim 1 wherein said bottom cap has a plurality of outside annular flanges, which are forced into engagement with said inward annular flange inside the flared opening bottom end of said barrel to prevent disconnection of said bottom cap from the bottom end of said barrel after the insertion of said bottom cap into the bottom end of said barrel invertedly.

6. The safety vacuum syringe for blood sampling of claim 1 wherein said bottom cap has a projecting portion, which is forced into engagement with the inward projecting portion of said barrel to prevent disconnection of said outer bottom cap from the bottom end of said barrel after the insertion of said outer bottom cap into the bottom end of said barrel invertedly.

* * * * *